United States Patent
McCulla et al.

(10) Patent No.: US 12,054,470 B2
(45) Date of Patent: Aug. 6, 2024

(54) PHOTOSWITCHABLE DIBENZOTHIENYLMETHYL TRIPHENYLPHOSPHONIUM DERIVATIVES AND METHODS OF TREATING CANCER THEREWITH

(71) Applicant: Saint Louis University, St. Louis, MO (US)

(72) Inventors: Ryan D. McCulla, St. Louis, MO (US); Ankita Isor, St. Louis, MO (US); Christopher Kent Arnatt, Manchester, MO (US)

(73) Assignee: Saint Louis University, St. Louis, MO (US)

( * ) Notice: Subject to any disclaimer, the term of this patent is extended or adjusted under 35 U.S.C. 154(b) by 909 days.

(21) Appl. No.: 17/046,885

(22) PCT Filed: Apr. 10, 2019

(86) PCT No.: PCT/US2019/026700
§ 371 (c)(1),
(2) Date: Oct. 12, 2020

(87) PCT Pub. No.: WO2019/199911
PCT Pub. Date: Oct. 17, 2019

(65) Prior Publication Data
US 2021/0147378 A1 May 20, 2021

Related U.S. Application Data

(60) Provisional application No. 62/656,121, filed on Apr. 11, 2018.

(51) Int. Cl.
| | |
|---|---|
| *C07D 333/76* | (2006.01) |
| *A61K 41/00* | (2020.01) |
| *A61K 45/06* | (2006.01) |
| *A61P 35/00* | (2006.01) |

(52) U.S. Cl.
CPC ........ *C07D 333/76* (2013.01); *A61K 41/0042* (2013.01); *A61K 45/06* (2013.01); *A61P 35/00* (2018.01)

(58) Field of Classification Search
CPC .. C07D 333/76; A61K 41/0042; A61K 45/06; A61P 35/00
See application file for complete search history.

(56) References Cited

PUBLICATIONS

Isor et al. Synthesis of (5-oxo-2-dibenzothienylmethyl) triphenylphosphonium and its localization in mitochondria to study oxidative stress, Saint Louis University, Poster. (Year: 2017).*
Kumar, Synthesis of trans-3, 4-dihydroxy-3, 4-dihydrophenanthro[3,2-b]-[1]benzothiophene, a potentially carcinogenic metabolite of sulfur heterocycle phenanthro[3,2-b][1]benzothiophene, J. Chem. Soc., 1, 1018-1023. (Year: 2001).*
Acheson et al., "The synthesis of thiophenium and of oxazolium salts from diazoketones," *Journal of the Chemical Society, Perkin I,* pp. 1185-1193, 1980.
Blanco et al., "Azobenzene-containing photoswitchable proteasome inhibitors with selective activity and cellular toxicity," *Bioorg. Med. Chem.,* 25(19):5050-5054, 2017.
Borowiak et al., "Photoswitchable Inhibitors of Microtubule Dynamics Optically Control Mitosis and Cell Death," *Cell,* 162(2):403-411, 2015.
Isor et al., "Synthesis of (5-oxo-2-dibenzothienylmethyl)triphenyl phosphonium and its localization in mitochondria to study oxidative stress," ACS—Midwest Regional Meeting, poster presented Oct. 20, 2017.
Jordan et al., "Tubulin as a target for anticancer drugs: agents which interact with the mitotic spindle," *Med. Res. Rev.,* 18(4):259-296, 1998.
Korang et al., "Photodeoxygenation of dibenzothiophene S-oxide derivatives in aqueous media," *J. Am. Chem. Soc.,* 132(12):4466-4476, 2010.
Kumar, "Synthesis of trans-3,4-dihydroxy-3,4-dihydrophenanthro[3,2-b]-[1]benzothiophene, a potentially carcinogenic metabolite of sulfur heterocycle phenanthrol[3,2-b][1]benzothiophene," *Journal of the Chemical Society, Perkin Trans. I,* 1:1018-1023, 2001.
Li et al., "Mitochondria-Targeting Polydopamine Nanoparticles to Deliver Doxorubicin for Overcoming Drug Resistance," *ACS Appl. Mater. Interfaces,* 9(20):16793-16802, 2017.
Nag et al., "Photochemistry of substituted dibenzothiophene oxides: the effect of trapping groups," *The Journal of Organic Chemistry,* 70:S1-S38, 2005.
PCT International Preliminary Report on Patentability issued in International Application No. PCT/US2019/026700, dated Oct. 22, 2020.
PCT International Search Report and Written Opinion issued in International Application No. PCT/US2019/026700, dated Aug. 27, 2019.
Pubmed Compound Summary for CID 101220329, 2015.
Pubmed Compound Summary for CID 11330146, 2006.
Qiao et al., "Synthesis, experimental and theoretical characterization, and field-effect transistor properties of a new class of dibenzothiophene derivatives: from linear to cyclic architectures," *Journal of Materials Chemistry,* 22:1313-1325, 2012.

(Continued)

*Primary Examiner* — Matthew P Coughlin
*Assistant Examiner* — Meghan C Heasley
(74) *Attorney, Agent, or Firm* — Parker Highlander PLLC

(57) ABSTRACT

In one aspect, the present disclosure provides a compound of the formula: In another aspect, the present disclosure also provides methods of preparing the compounds disclosed herein. In another aspect, the present disclosure also provides pharmaceutical compositions and methods of use of the compounds disclosed herein.

(I)

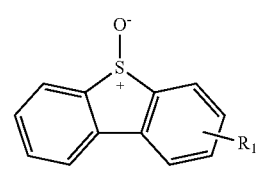

18 Claims, 9 Drawing Sheets

(56) References Cited

PUBLICATIONS

Ross et al., "Lipophilic triphenylphosphonium cations as tools in mitochondrial bioenergetics and free radical biology," *Biochemistry. (Mosc).*, 70(2):222-230, 2005.

Sheldon et al., "Photoswitchable anticancer activity via trans-cis isomerization of a combretastatin A-4 analog," *Org. Biomol. Chem.*, 14(1):40-49, 2016.

Szymanski et al., "Light-Controlled Histone Deacetylase (HDAC) Inhibitors: Towards Photopharmacological Chemotherapy," *Chemistry*, 21(46):16517-16524, 2015.

Throgmorton et al., "Synthesis of Unsymmetric Monosubstituted and Disubstituted Dinaphthothiophenes," *J. Heterocycl. Chem.*, 54(6):e3002, pp. 3682-3688, 2017.

Trnka et al., "Lipophilic triphenylphosphonium cations inhibit mitochondrial electron transport chain and induce mitochondrial proton leak," *PLoS One*, 10(4):e0121837, 2015.

Zheng et al., "Photodeoxygenation of dinaphthothiophene, benzophenanthrothiophene, and benzonaphthothiophene S-oxides," *Photochem. Photobiol. Sci.*, 15(6):791-800, 2016.

\* cited by examiner

PHOTOSWITCHABLE DIBENZOTHIENYLMETHYL TRIPHENYLPHOSPHONIUM DERIVATIVES AND METHODS OF TREATING CANCER THEREWITH

This application claims the benefit of priority to U.S. Provisional Application Ser. No. 62/656,121, filed on Apr. 11, 2018, the entirety of which is hereby incorporated by reference.

BACKGROUND

1. Field

This disclosure relates to the fields of medicine, pharmacology, chemistry, and oncology. In particular, new compounds, compositions, methods of treatment, and methods of synthesis relating to derivatives of dibenzothiophene-S-oxide (DBTO) are disclosed.

2. Related Art

Photoswitchable activity of small molecules has been reported in recent literature for efficient and targeted cancer therapy (Sheldon et al., 2016; Borowiak et al., 2016 and Szymanski et al., 2015). Photostatins are small molecule inhibitors that interfere with microtubule dynamics in a cell that ultimately lead to pro-apoptotic and anti-mitotic effects (Jordan et al., 1998). Photostatins that can now be optically controlled have been reported in the literature where their cytotoxicity increases by 250 times more when illuminated with blue light (Borowiak et al., 2015). Similar studies on drugs with a photoswitchable azobenzene component within the structure are promising candidates for targeted photodynamic chemotherapy (Sheldon et al., 2016; Szymanski et al., 2015 and Blanco et al., 2017).

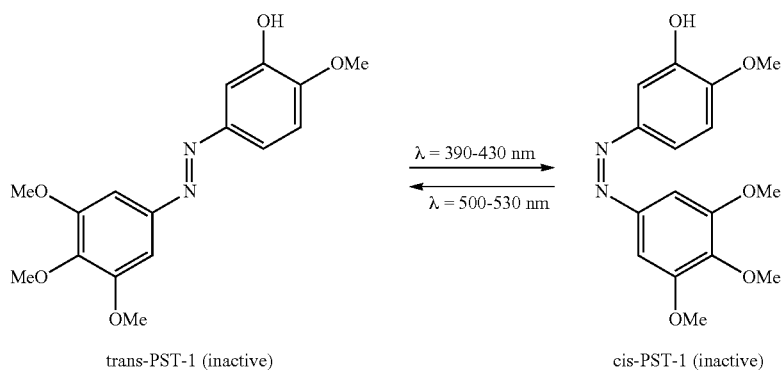

Scheme 1: Photoswitchable activity of PST-1 where only the cis form has the CDI pharmacophore responsible for pro-aptotic effects (Borowiak et al., 2015).

trans-PST-1 (inactive)      cis-PST-1 (inactive)

In recent years, the inventor's lab has synthesized several heterocyclic sulfur containing aromatic compound (DBTO) derivatives that undergo photodeoxygenation on UV-A irradiation (Zheng et al., 2016; Korang et al., 2010 and Throgmorton et al., 2017). Lipophilic triphenylphosphonium cationic molecules have been speculated to accumulate in mitochondria due to its negative membrane potential (Trnka et al., 2015; Li et al., 2017 and Ross et al., 2005). There is evidence in the literature that they disrupt the membrane potential and inhibit the mitochondrial electron transport chain (Trnka et al., 2015). The inventor's lab has synthesized a water soluble heterocyclic aromatic compound, (5-oxo-2-dibenzothienylmethyl)triphenylphosphonium, which on UV-A irradiation undergoes photodeoxygenation to yield a lipophilic triphenylphosphonium compound that has been shown to be toxic to cells.

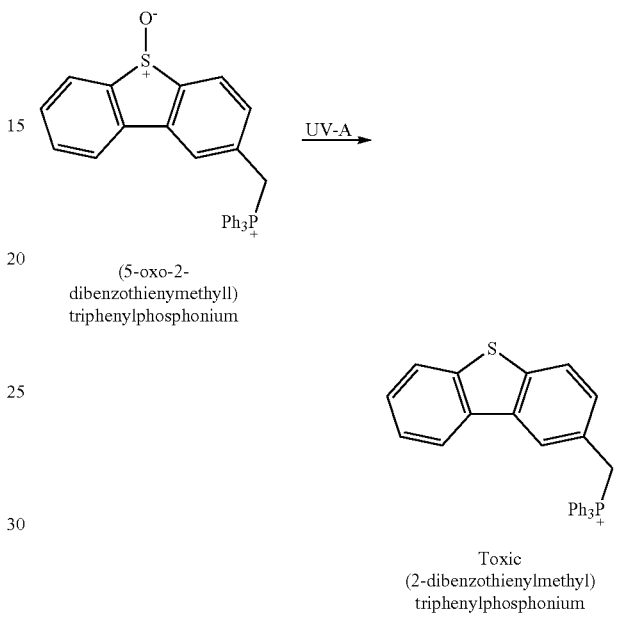

Scheme 2: Toxic lipophilic cation being produced on photodeoxygenation of (5-oxo-2-dibenzothienylmethyl)triphenyl phosphonium on UV-A irradiation.

(5-oxo-2-dibenzothienymethyll) triphenylphosphonium

Toxic (2-dibenzothienylmethyl) triphenylphosphonium

SUMMARY

In some aspects, the present disclosure provides compounds of formula:

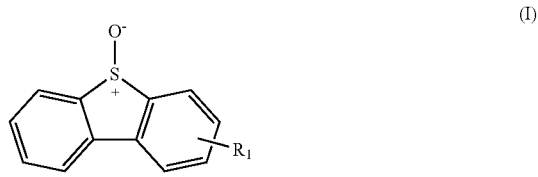

(I)

wherein:

R$_1$ is —Y$_1$—R$_2$; wherein:

Y$_1$ is alkanediyl$_{(C\leq6)}$, substituted alkanediyl$_{(C\leq6)}$, or a linker of the formula:

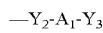

wherein:

Y$_2$ and Y$_3$ are each independently alkanediyl$_{(C\leq6)}$ or substituted alkanediyl$_{(C\leq6)}$;

A$_1$ is —C(O)O— or —C(O)NH—; and

R$_2$ is P(R$_3$)(R$_3$')(R$_3$")$^+$X$_1$$^-$; wherein:

R$_3$, R$_3$', and R$_3$" are each independently aryl$_{(C\leq12)}$ or substituted aryl$_{(C\leq12)}$; and X$_1$$^-$ is a monovalent anion;

or a pharmaceutically acceptable salt thereof.

In some embodiments, the compounds are further defined as:

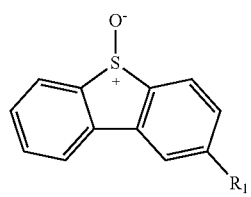
(II)

wherein:

R$_1$ is —Y$_1$—R$_2$; wherein:

Y$_1$ is alkanediyl$_{(C\leq6)}$ or substituted alkanediyl$_{(C\leq6)}$; and

R$_2$ is P(R$_3$)(R$_3$')(R$_3$")$^+$X$_1$$^-$; wherein:

R$_3$, R$_3$', and R$_3$" are each independently aryl$_{(C\leq12)}$ or substituted aryl$_{(C\leq12)}$; and X$_1$$^-$ is a monovalent anion;

or a pharmaceutically acceptable salt thereof.

In some embodiments, Y$_1$ is alkanediyl$_{(C\leq6)}$, such as methylene. In other embodiments, Y$_1$ is a linker of the formula: —Y$_2$-A$_1$-Y$_3$. In some embodiments, Y$_2$ is alkanediyl$_{(C\leq6)}$, such as methylene. In some embodiments, Y$_3$ is alkanediyl$_{(C\leq6)}$, such as methylene. In some embodiments, A$_1$ is —C(O)O—. In some embodiments, R$_3$, R$_3$', and R$_3$" are each independently aryl$_{(C\leq12)}$, such as R$_3$, R$_3$', and R$_3$" are each phenyl. In some embodiments, X$_1$$^-$ is halide, such as bromide. In some embodiments, the compound is further defined as:

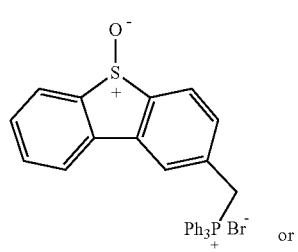
or

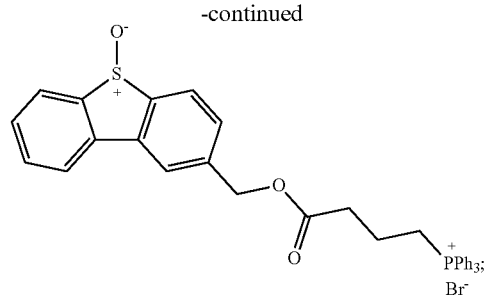

or a pharmaceutically acceptable salt thereof.

In another aspect, the present disclosure provides methods of making a compound of formula:

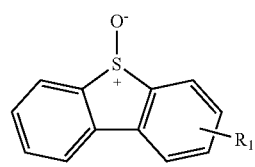
(I)

wherein:

R$_1$ is —Y$_1$—R$_2$; wherein:

alkanediyl$_{(C\leq6)}$, substituted alkanediyl$_{(C\leq6)}$, or a linker of the formula:

wherein:

Y$_2$ and Y$_3$ are each independently alkanediyl$_{(C\leq6)}$ or substituted alkanediyl$_{(C\leq6)}$;

A$_1$ is —C(O)O— or —C(O)NH—; and

R$_2$ is P(R$_3$)(R$_3$')(R$_3$")+X$_1$$^-$; wherein:

R$_3$, R$_3$', and R$_3$" are each independently aryl$_{(C\leq12)}$ or substituted aryl$_{(C\leq12)}$; and X$_1$$^-$ is a monovalent anion;

comprising:

(A) reacting a compound of the formula:

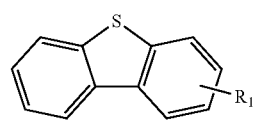
(III)

wherein:

R$_1$ is —Y$_1$—R$_2$; wherein:

Y$_1$ is alkanediyl$_{(C\leq6)}$, substituted alkanediyl$_{(C\leq6)}$, or a linker of the formula:

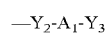

wherein:

Y$_2$ and Y$_3$ are each independently alkanediyl$_{(C\leq6)}$ or substituted alkanediyl$_{(C\leq6)}$;

A$_1$ is —C(O)O— or —C(O)NH—; and

R$_2$' is halo;

in the presence of an oxidizing agent to form a compound of the formula:

(I)

wherein:
  $R_1$ is —$Y_1$—$R_2$; wherein:
    $Y_1$ is alkanediyl$_{(C≤6)}$, substituted alkanediyl$_{(C≤6)}$, or a linker of the formula:

—$Y_2$-$A_1$-$Y_3$ wherein:
      $Y_2$ and $Y_3$ are each independently alkanediyl$_{(C≤6)}$ or substituted alkanediyl$_{(C≤6)}$;
      $A_1$ is —C(O)O— or —C(O)NH—; and
      $R_2'$ is halo; and
(B) reacting the compound prepared in step A with a compound of the formula:

P($R_3$)($R_3'$)($R_3''$)

wherein:
      $R_3$, $R_3'$, and $R_3''$ are each independently aryl$_{(C≤12)}$ or substituted aryl$_{(C≤12)}$.

In some embodiments, $R_2'$ is bromide. The methods may further comprise a solvent. In some embodiments, the solvent used in Step A is a haloalkane, such as dichloromethane. In some embodiments, the solvent used in Step B is an arene, such as toluene. In some embodiments, Step A is run at a reduced temperature, such as from about −80° C. to about 20° C. In some embodiments, the reduced temperature starts at about −50° C. and is raised to about 0° C. In some embodiments, Step B is run at an elevated temperature, such as a temperature sufficient to cause the solvent to reflux.

In still another aspect, the present disclosure provides compounds of the formula:

(III)

wherein:
  $R_4$ is —$Y_4$—$R_5$; wherein:
    $Y_4$ is alkanediyl$_{(C≤6)}$, substituted alkanediyl$_{(C≤6)}$, or a linker of the formula:

—$Y_5$-$A_2$-$Y_6$ wherein:
      $Y_5$ and $Y_6$ are each independently alkanediyl$_{(C≤6)}$ or substituted alkanediyl$_{(C≤6)}$;
      $A_2$ is —C(O)O— or —C(O)NH—; and
    $R_5$ is P($R_6$)($R_6'$)($R_6''$)$^+$$X_2^-$; wherein:
      $R_6$, $R_6'$, and $R_6''$ are each independently aryl$_{(C≤12)}$ or substituted aryl$_{(C≤12)}$; and
      $X_2^-$ is a monovalent anion;
or a pharmaceutically acceptable salt thereof.
In some embodiments, the compounds are further defined as:

(IV)

wherein:
  $R_4$ is —$Y_4$—$R_5$, wherein:
    $Y_4$ is alkanediyl$_{(C≤6)}$ or substituted alkanediyl$_{(C≤6)}$; and
    $R_5$ is P($R_6$)($R_6'$)($R_6''$)$^+$$X_2^-$; wherein:
      $R_6$, $R_6'$, and $R_6''$ are each independently aryl$_{(C≤12)}$ or substituted aryl$_{(C≤12)}$; and
      $X_2^-$ is a monovalent anion;
or a pharmaceutically acceptable salt thereof.

In some embodiments, $Y_4$ is alkanediyl$_{(C≤6)}$, such as methylene. In other embodiments, $Y_4$ is a linker of the formula: —$Y_5$-$A_2$-$Y_6$. In some embodiments, $Y_5$ is alkanediyl$_{(C≤6)}$, such as methylene. In some embodiments, $Y_6$ is alkanediyl$_{(C≤6)}$, such as methylene. In some embodiments, $A_2$ is —C(O)O—. In some embodiments, $R_6$, $R_6'$, and $R_6''$ are each independently aryl$_{(C≤12)}$, such as when $R_6$, $R_6'$, and $R_6''$ are each phenyl. In some embodiments, $X_2^-$ is halide, such as bromide. In some embodiments, the compound is further defined as:

Ph$_3$P$^+$ Br$^-$    or

PPh$_3^+$; Br$^-$ or a pharmaceutically acceptable salt thereof.

In yet another aspect, the present disclosure provides pharmaceutical compositions comprising a compound described herein and an excipient. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion.

In still yet another aspect, the present disclosure provides methods of treating a cancer in a patient in need thereof comprising (a) administering to the patient a therapeutically effective amount of a compound or composition described herein, and (b) exposing a cancer cell in said patient to UV-A light. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the methods further comprise administering a second therapy such as surgery, a second chemotherapeutic, radiotherapy, or immunotherapy. In some embodiments, the patient is a mammal, such as a human. In some embodiments, the compound is administered once. In other embodiments, the compound is administered two or more times. In some embodiments, the UV-A light is 320-400 nm light.

In still another aspect, the present disclosure provides methods of treating a cancer in a patient in need thereof comprising administering to the patient a therapeutically effective amount of a compound or composition described herein. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the methods further comprise administering a second therapy such as surgery, a second chemotherapeutic, radiotherapy, or immunotherapy. In some embodiments, the patient is a mammal such as a human. In some embodiments, the compound is administered once. In other embodiments, the compound is administered two or more times.

It is contemplated that any method or composition described herein can be implemented with respect to any other method or composition described herein. For example, a compound synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

DESCRIPTION OF ILLUSTRATIVE EMBODIMENTS

Figure 1:
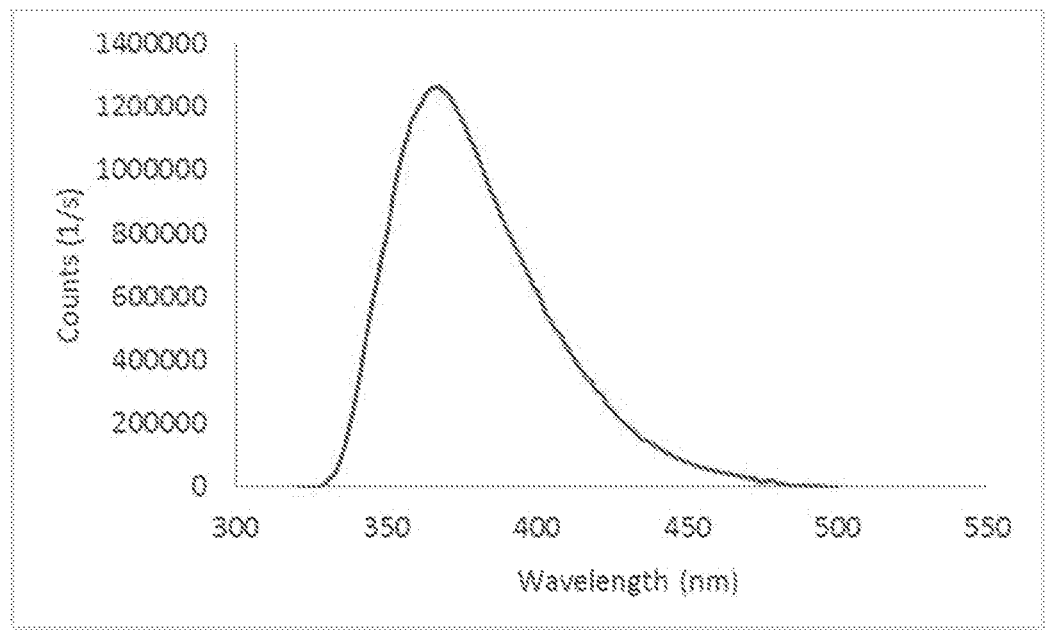
FIG. 1. Fluorescence spectrum of 0.1 mM of (5-dioxo-2-dibenzothienylmethyl)triphenylphosphonium in acetonitrile. Excitation was carried out at 300 nm. No fluorescence was observed when excited at 400 nm.

As discussed above, reactive oxygen species present significant potential as anti-cancer agents, but at present suffer from certain limitations in terms of delivery and targeting. The inventors noted that triphenylphosphonium had been identified as a cationic ligand that can concentrate in mitochondria which has a negative membrane potential. The inventors focused on synthesizing a water soluble version of dibenzothiophene-S-oxide (DBTO) with triphenylphosphonium as a substituent, thereby permitting this DBTO derivative to permeate the cell membrane due to its lipophilicity and concentrate in mitochondria. This not only allows one to better study the effects of oxidative stress in cellular signaling in mitochondria, but renders this compound far more useful than its predecessor in terms of a therapeutic. This compound, and methods of synthesis and therapy are described in more detail below.

I. COMPOUNDS AND FORMULATIONS THEREOF

The compound provided by the present disclosure is shown, for example, above in the summary section and in the Examples and claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The compound described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. The compound may occur as racemates and racemic mixtures, single enantiomers, diastereomeric mixtures and individual diastereomers. In some embodiments, a single diastereomer is obtained. The chiral centers of the compounds of the present disclosure can have the (S) or the (R) configuration.

Chemical formulas used to represent the compound described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The compound described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compound described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The compound described herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compound of the present disclosure as well as methods of delivering the compound. The compound described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compound can form complexes with solvents in which they are reacted or from which they are precipitated or crystallized. These complexes are known as "solvates." For example, a complex with water is known as a "hydrate." Solvates of the compound described herein are within the scope of the disclosure. It will also be appreciated by those skilled in organic chemistry that many organic compound can exist in more than one crystalline form. For example, crystalline form may vary from solvate to solvate. Thus, all crystalline forms of the compound described herein are within the scope of the present disclosure.

In some embodiments of the present disclosure, the compound is included a pharmaceutical formulation. Materials for use in the preparation of microspheres and/or microcapsules are, e.g., biodegradable/bioerodible polymers such as polygalactin, poly(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the compound described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

A. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof in a divalent context "phosphate" means —OP(O)(OH)O— or a deprotonated form thereof "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example,

 ,  , 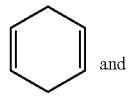 and

 .

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿", when drawn perpendicularly across a bond (e.g.,

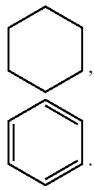

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⦀⦀" means a single bond where the group attached to the thick end of the wedge is "into the page". The symbol "⦀⦀" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

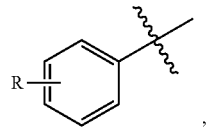

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

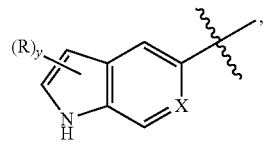

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group.

Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of ketoenol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, A, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

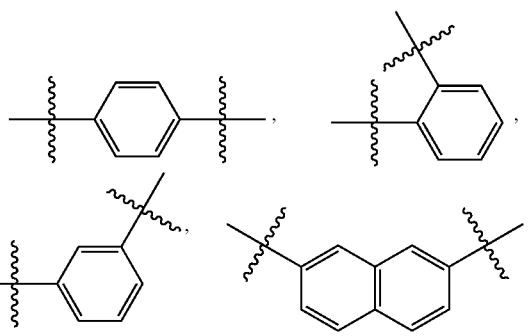

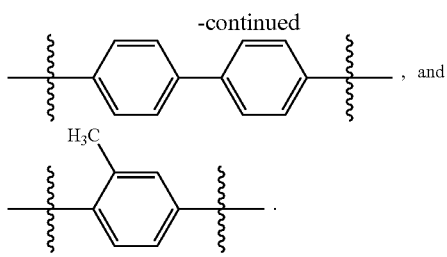
, and

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

II. CANCER AND OTHER HYPERPROLIFERATIVE DISEASES

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the compound described herein may be used to lead to decreased cell counts and as such can potentially be used to treat a variety of types of cancer lines. In some aspects, it is anticipated that the compound described herein may be used to treat virtually any malignancy.

Cancer cells that may be treated with the compound of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the compound of the present disclosure is contemplated. Generally, this will entail preparing compositions that are essentially free of pyrogens, as well as other impurities that could be harmful to humans or animals.

One will generally desire to employ appropriate salts and buffers to render the compound stable and allow for uptake by target cells. Buffers also will be employed when recombinant cells are introduced into a patient. Aqueous compositions of the present disclosure comprise an effective amount of the compound to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the compound of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compound may also be administered parenterally or intraperitoneally. Solutions of the active compound as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the compound described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 mL of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate regulatory agencies for the safety of pharmaceutical agents.

B. Methods of Treatment

In particular, the compositions that may be used in treating cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation. In some embodiments, amounts of the compound used to induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the compound may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the compound described herein may be used in combination therapies with one or more cancer therapies or a compound which mitigates one or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with the compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the compound described herein may precede or follow the other treatment by intervals ranging from minutes to weeks. One would generally ensure that a significant period of time did not expire between the times of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where the compound of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are also contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin $\gamma_1$ and calicheamicin on; dynemicin, including dynemicin A; uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, or zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 12.9 to 51.6 mC/kg for prolonged periods of time (3 to 4 wk), to single doses of 0.516 to 1.55 C/kg. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides, et al., 1998), cytokine therapy, e.g., interferons α, β, and γ; IL-1, GM-CSF and TNF (Bukowski, et al., 1998; Davidson, et al., 1998; Hellstrand, et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras, et al., 1998; Hanibuchi, et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton, et al., 1992; Mitchell, et al., 1990; Mitchell, et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg, et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 41.1° C.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate pharmaceutical agent regulatory agencies.

It also should be pointed out that any of the foregoing therapies may prove useful by themselves in treating cancer.

IV. SYNTHETIC METHODS

In some aspects, the compound of this disclosure can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein. The synthetic method described herein may be used to produce preparative scale amounts of the compound described herein.

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Photoactivatable Precursors, Synthesis and Localization in Mitochondria (FIG. 1)

The available bromo dibenzothiophene was formylated using an alkyllithium and DMF to generate a formyl dibenzothiophene. The formyl dibenzothiophene was reduced with a borohydride reagent to generate the primary alcohol dibenzothiophene. The primary alcohol was converted using hydrobromic acid in acetic acid to generate a bromomethyl dibenzothiophene. The bromomethyl dibenzothiophene was oxidized to form the sulfone which was then reacted with a phosphine which underwent nucleophilic displacement to generate the resultant final product (2-TPPMDBTO).

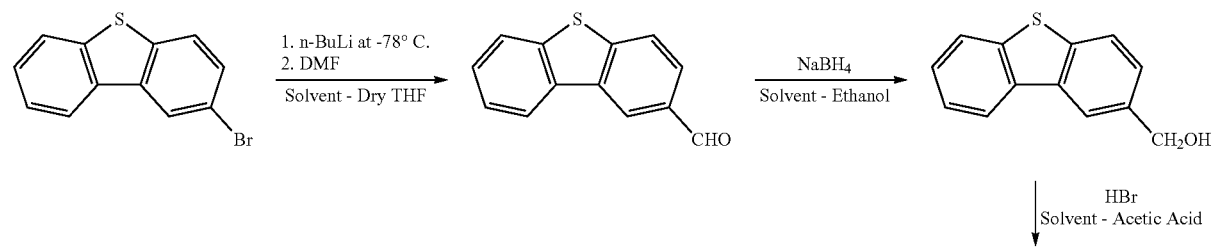

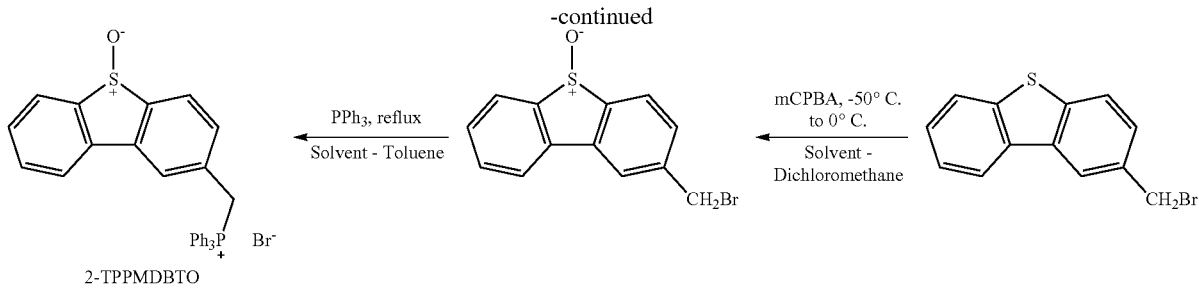

2-TPPMDBTO

Scheme 4 - Synthetic scheme for the synthesis of MA-3

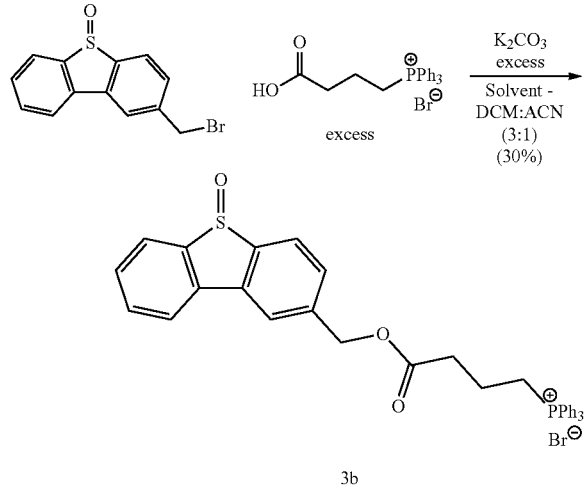

The product precipitated in toluene and was filtered. Purity was determined by HPLC analysis of the precipitated product dissolved in acetonitrile. The product was 95.524% pure. Similar synthetic scheme was followed to synthesize the sulfone derivative except in Step 4, the oxidation was carried out at room temperature. The sulfone derivative fluoresces on UV-A excitation. The inventors are making efforts to use this property to observe and image the sulfone derivative localizing in mitochondria using a microscope.

On photolysis of the above synthesized molecule using UV-A, the photoproduct is generated.

Example 2—Characterization

The molecule was characterized using Low Res MS, $^1$H-NMR, UV-Vis and the purity was tested on HPLC. The NMR experiments were performed on Bruker 400 MHz instrument, LCMS was recorded on a LCMS-2010 EV, UV-Vis analysis was performed using a Shimadzu UV-1800 using a 10 mm quartz cuvette. HPLC analyses were performed on Agilent 1200 series HPLC fitted with a DAD and an Agilent Eclipse XDB-C18 column.

$^1$H NMR (400 MHz, DMSO)' Impurity—Water (3.31 ppm);

8.08 (d, J=7.6 Hz, 1H), 8.00 (d, J=8.0 Hz, 1H), 7.90-7.94 (m, 3H), 7.68-7.78 (m, 13H), 7.60 (t, J=7.5 Hz, 1H), 7.53 (d, J=7.6 Hz, 1H), 7.45 (s, 1H), 7.23 7.23 (d, J=7.9 Hz, 1H), 5.32 (d, J=16 Hz, 2H),

Low Res MS (positive mode): m/z [M]+ calcd for $C_{31}H_{24}OPS^+$=475.57. Found: 475.

Figure 2:
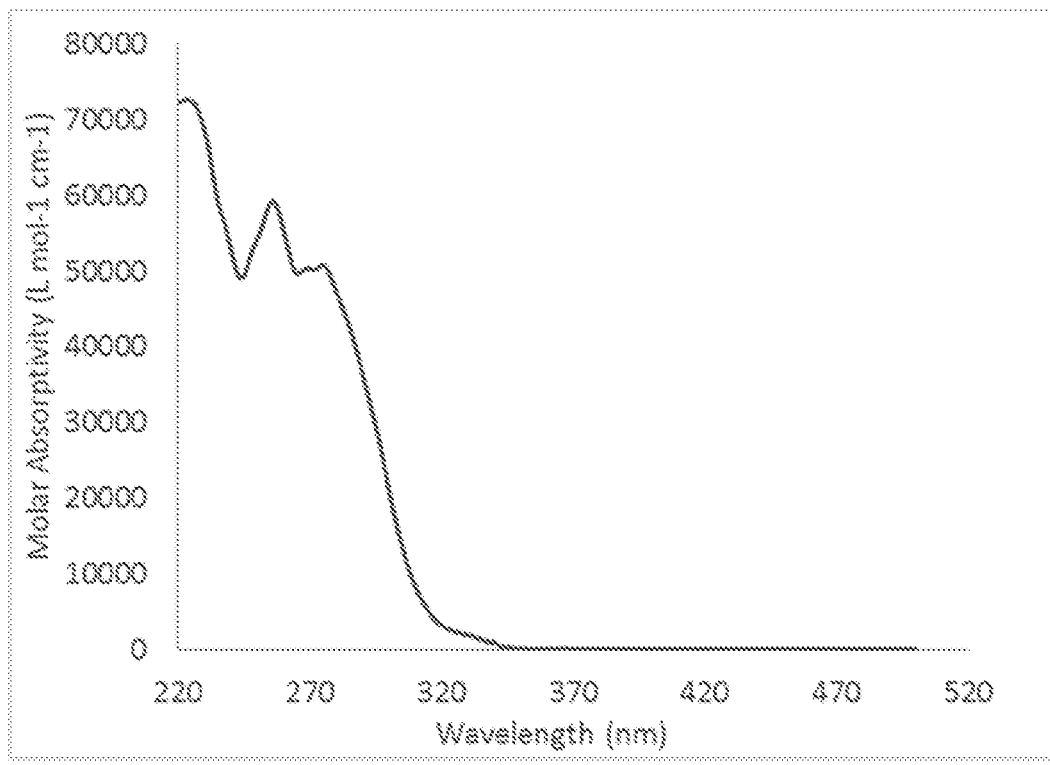
FIG. 2. UV-Vis spectrum of 2-TPPMDBTO in acetonitrile.
Figure 3:
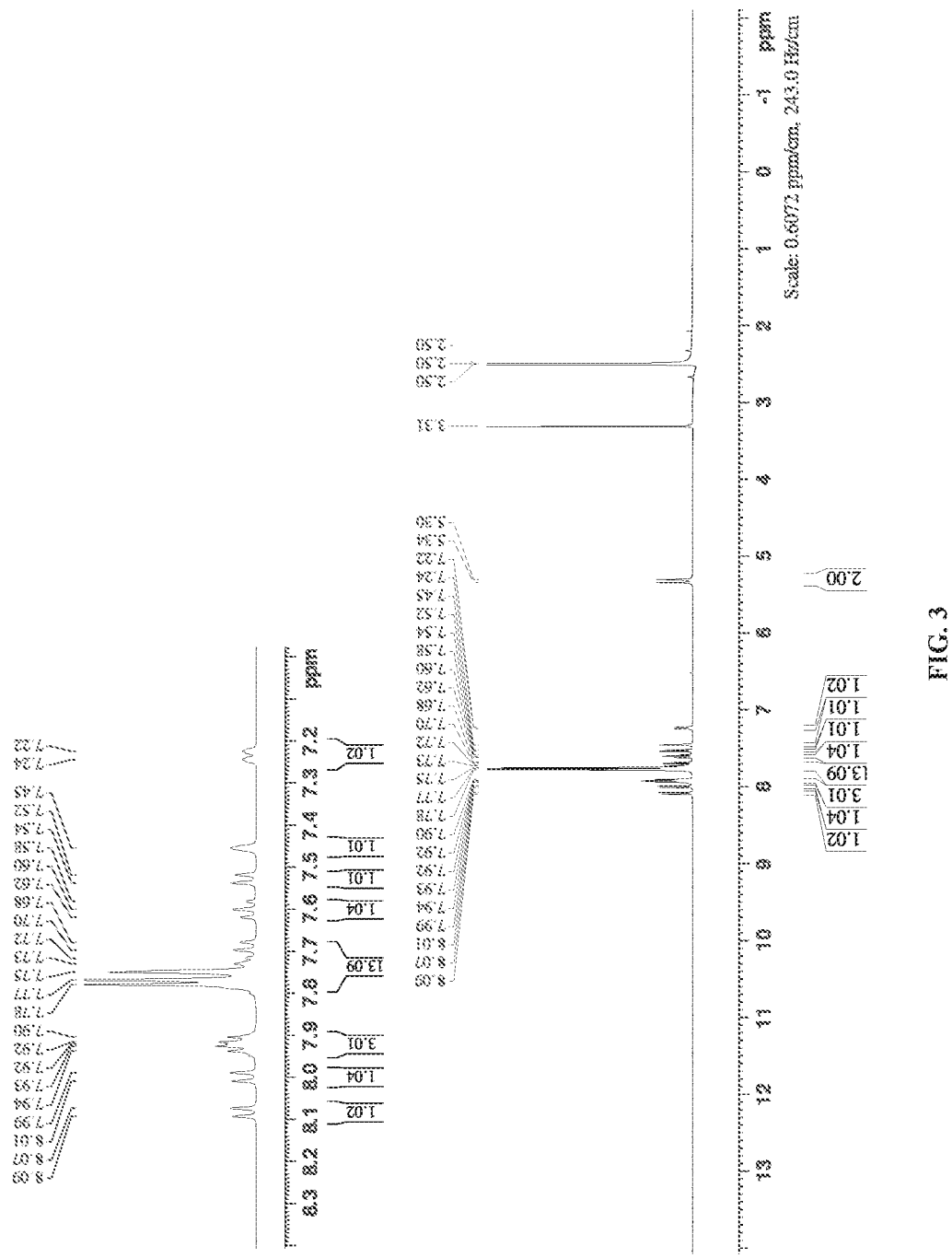
FIG. 3. $^1$H-NMR (400 MHz, DMSO)' Impurity—Water (3.31 ppm); $\delta$=5.32 (d, J=16 Hz, 2H), 7.23 (d, J=7.9 Hz, 1H), 7.45 (s, 1H), 7.53 (d, J=7.6 Hz, 1H), 7.60 (t, J=7.5 Hz, 1H), 7.68-7.78 (m, 13H), 7.90-7.94 (m, 3H), 8.00 (d, J=8.0 Hz, 1H), 8.08 (d, J=7.6 Hz, 1H).
Figure 4:
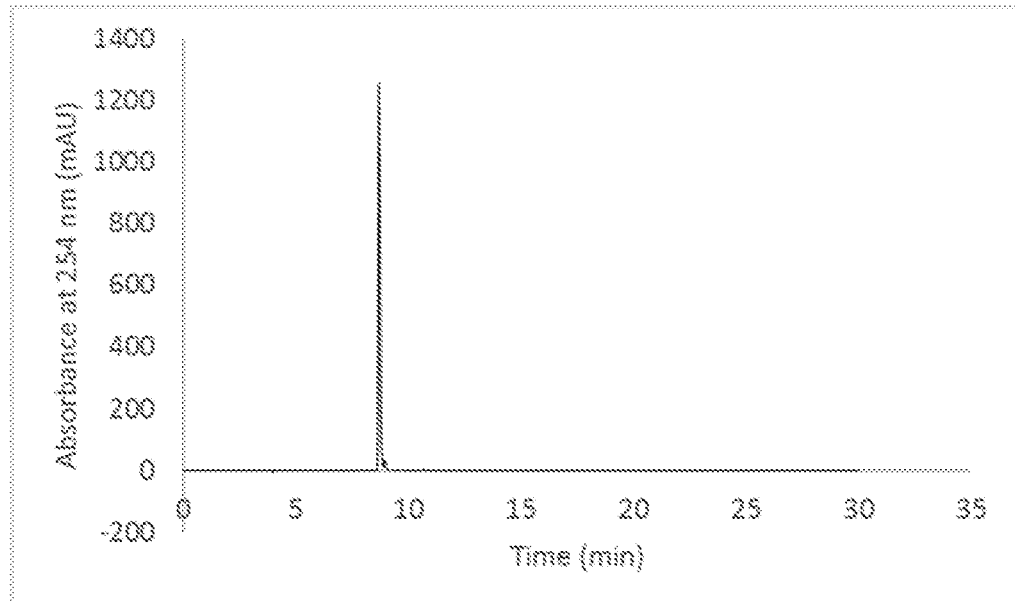
FIG. 4. HPLC purity trace showing absorbance at 254 nm.

UV-Vis spectrum is shown in FIG. 2. The HPLC purity trace is shown in FIG. 4.

Example 3—Cell Studies

Figure 5:
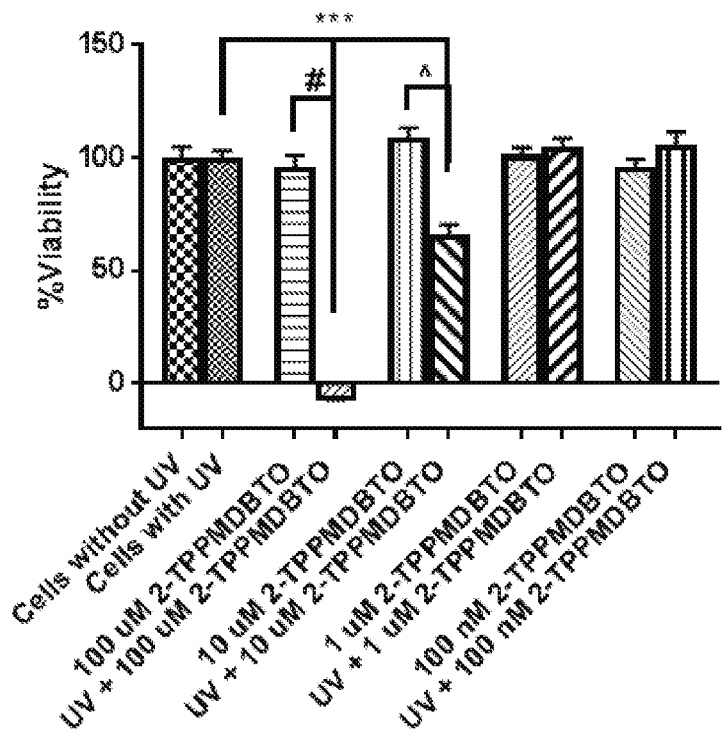
FIG. 5. Cell viability assay of 2-TPPMDBTO in MDA-MB-231 with and without exposure to UV-A light. ***—cells with UV vs. UV_100 μM 2-TPPMDBTO, p<0.0001; #—100 μM 2-TPPMDBTO vs. UV_100 μM 2-TPPMDBTO, p<0.0001; ^—10 μM 2-TPPMDBTO vs. UV+10 μM 2-TPPMDBTO, p<0.0001.

As shown in FIG. 5, MDA-MB-231 breast cancer cells were plated at 10,000 cells/well on two 96 well plates. After 24 hours incubation at 37° C., varying concentrations of 2-TPPMDBTO were added and incubated for 1 hour at 37° C. One plate with cells were then left at room temperature covered for 15 minutes (cells without UV). The second plate was exposed to UV-A in a Luzchem photoreactor with 8 LZC-UVA lamps for 15 minutes (Cells with UV). Plates were then incubated for 24 hours at 37° C. and then a MTS cell viability assay (Promega) was performed. Cell viability assay was run on a Flexstation3 mulitmode plate reader and percent viability was calculated. Statistical analyses were performed using GraphPad Prism program.

Figure 6A:
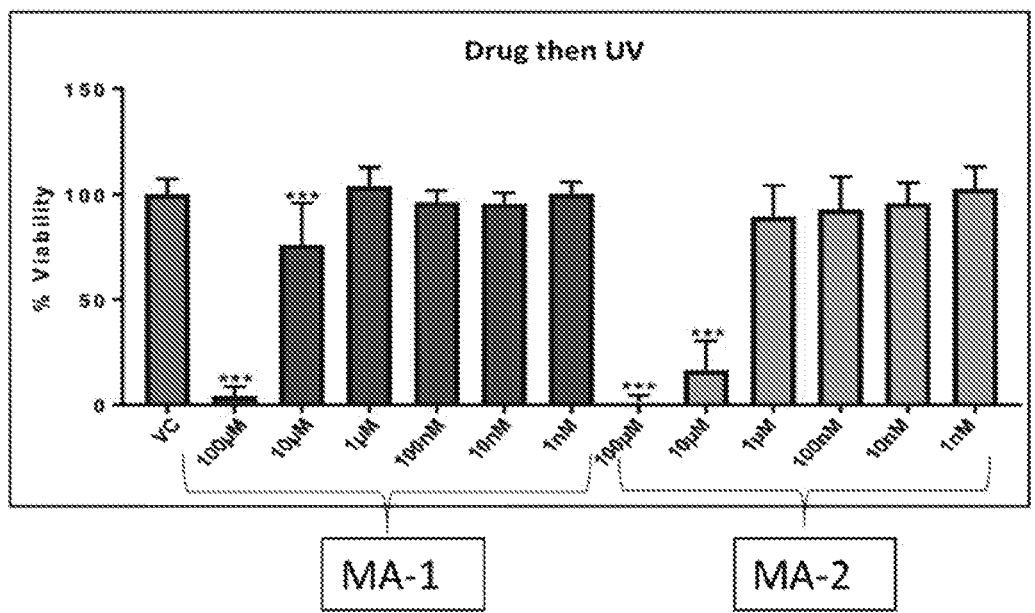
FIGS. 6A-C. MA-1 due to S—O bond cleavage produces MA-2 when exposed to UV-A (Addition of compound pre-UV exposure) and decrease in % cell viability is observed for that plate for 100 μM and 10 μM drug concentrations. For all the three UV-exposure conditions we observe that MA-2 decreases % cell viability. [*—p<0.005, ***—p<0.0005, when compared to the VC where n=4].
Figure 6B:
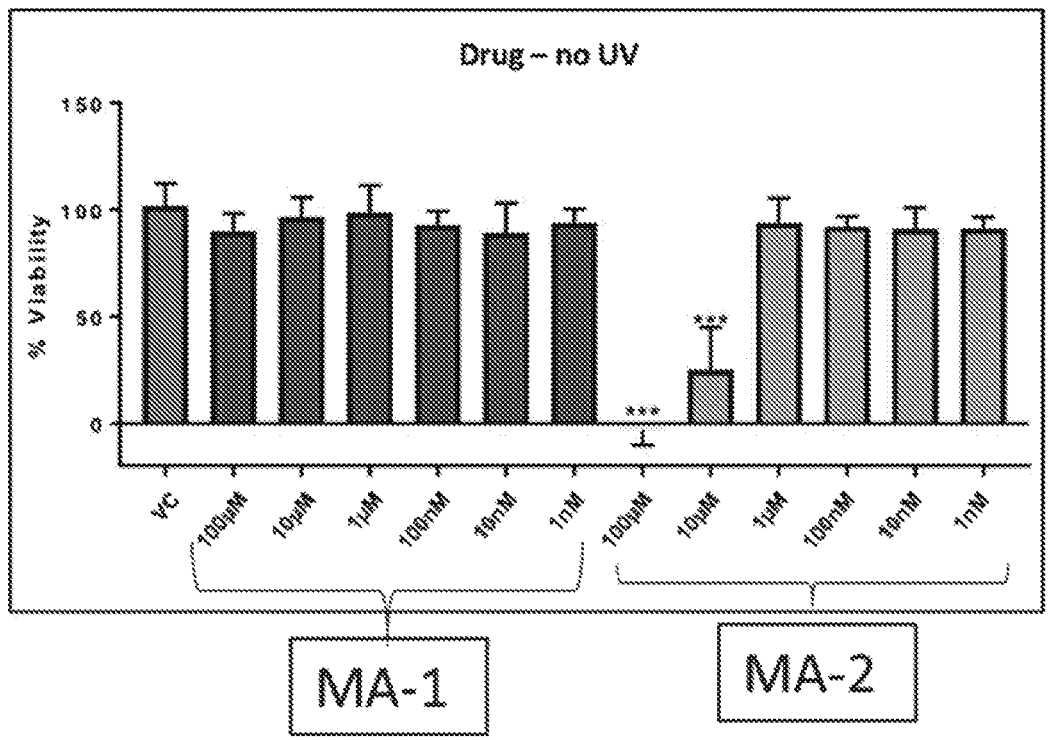
Figure 6C:
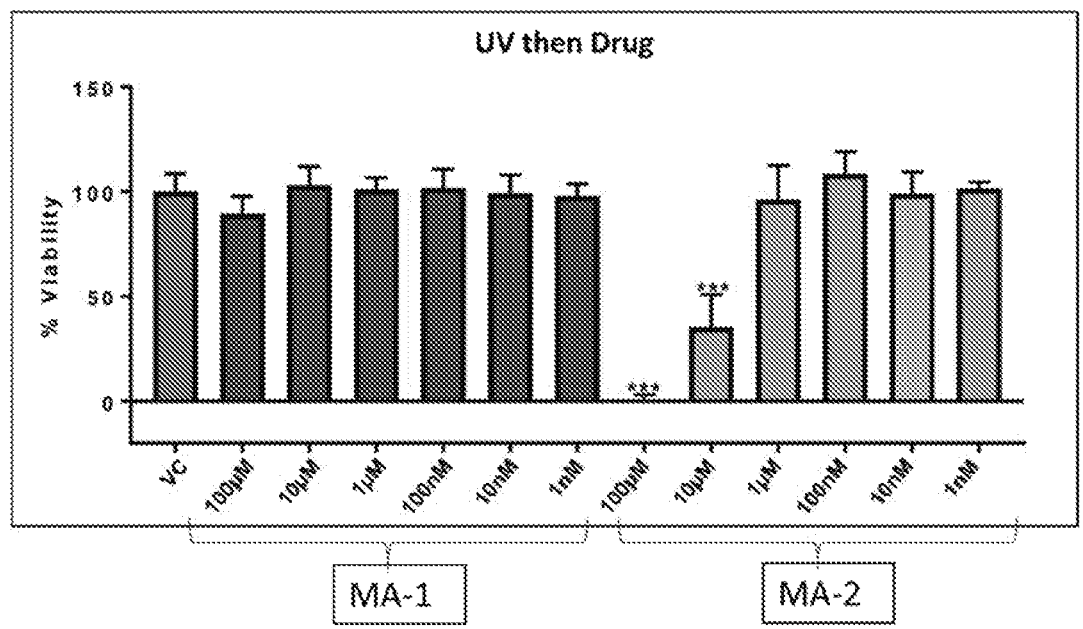
Figure 7A:
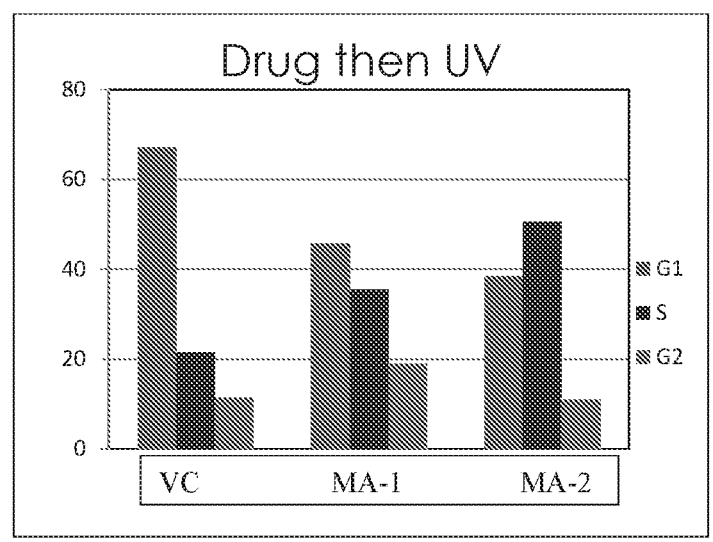
FIGS. 7A-7C. Compounds 1a and 1b shows to presence of UV-A irradiation is necessary to lead to cell cycle arrest. When the drug is administered after irradiation or without irradiation, no significant change in the progress was seen.
Figure 7B:
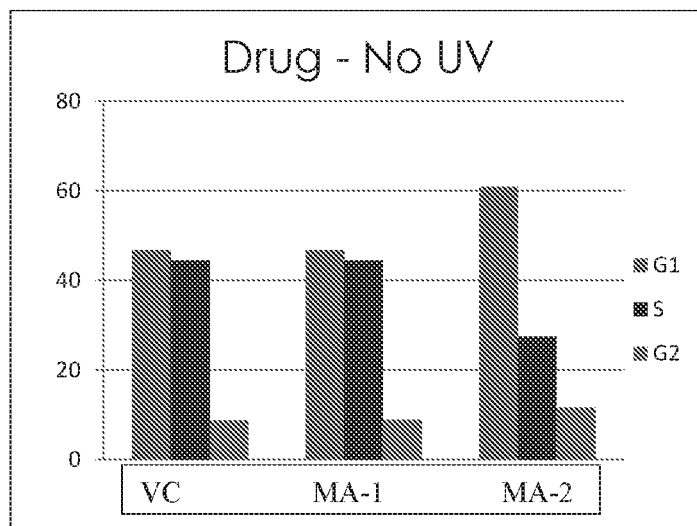
Figure 7C:
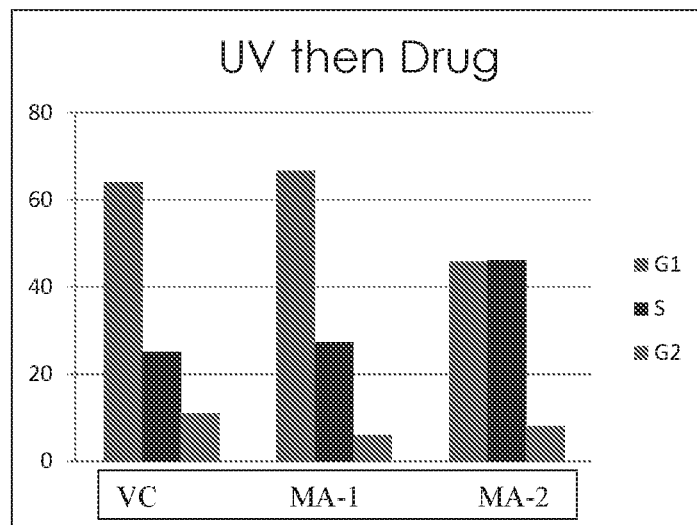
Figure 9A:
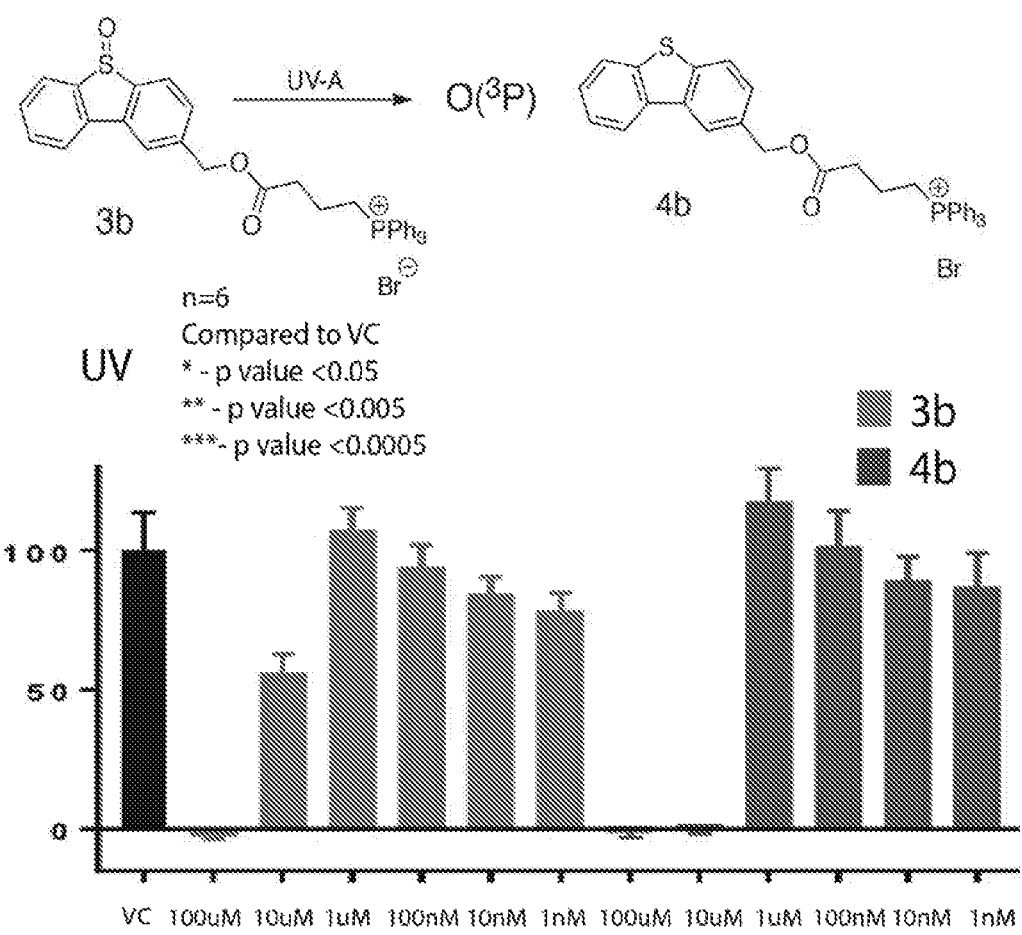
FIGS. 9A-9C. Compound 3b was analyzed to determine the requirement of UV-A irradiation to obtain an active compound.
Figure 9B:
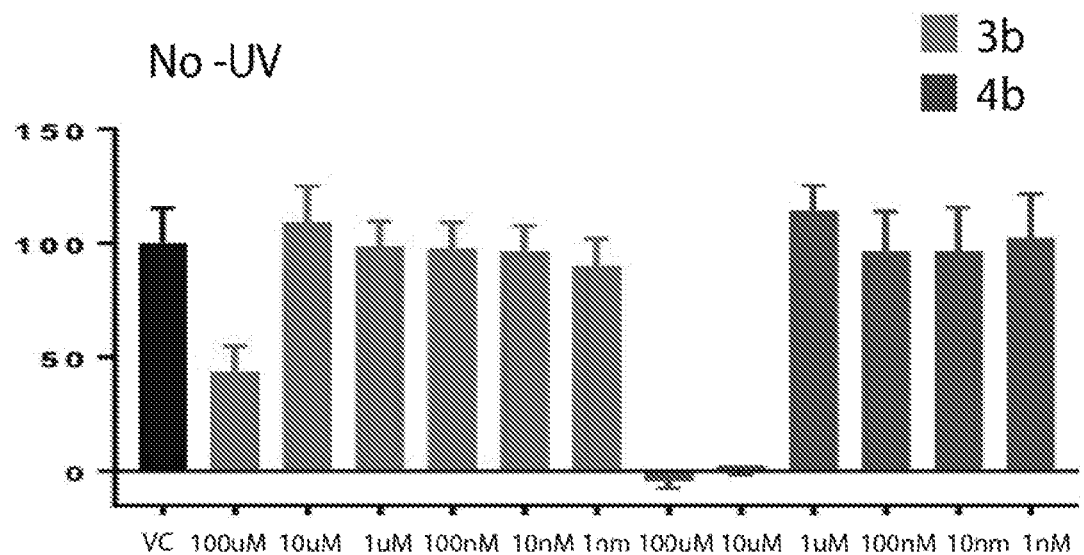
Figure 9C:
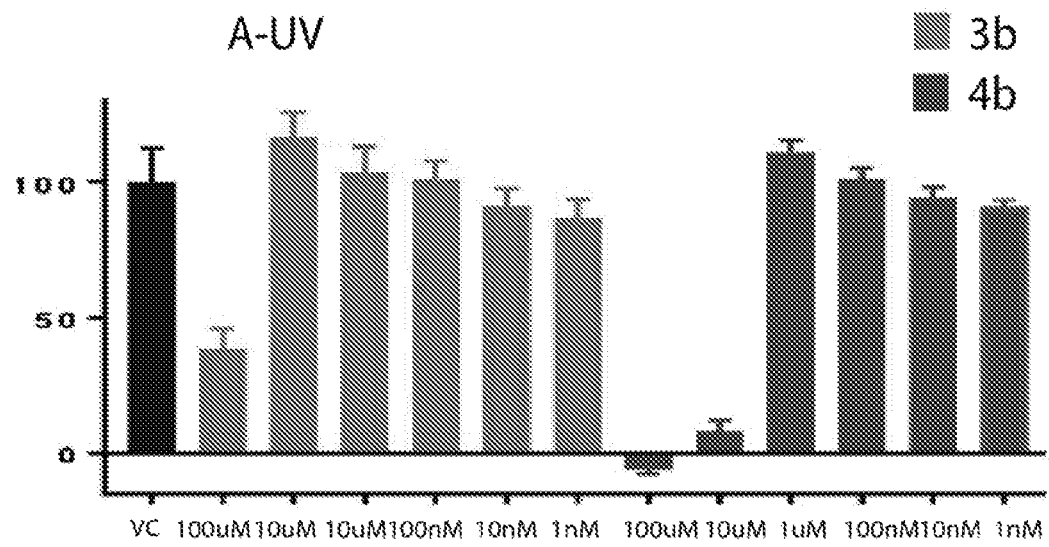

FIGS. 6A-C show cell studies wherein MDA-MB-231 breast cancer cells were plated at 10,000 cells/well on three 96 well plates. After 24 hours incubation at 37° C., varying concentrations of MA-1 and MA-2 were added and incubated for 1 hour at 37° C. on only two plates (pre-UV and no UV exposure). One plate with cells were then left at room temperature covered for 30 min (no UV). The second plate (pre-UV) and the third plate (post-UV) were exposed to UV-A in a Luzchem photoreactor with 8 LZC-UVA lamps for 30 min. Varying concentrations of MA-1, MA-2, MA-3 and MA-4 were added to post UV plate after irradiation. Plates were then incubated for 24 hours at 37° C. and then a MTS cell viability assay (Promega) was performed. Cell viability assay was run on a Flexstation3 mulitmode plate reader and percent viability was calculated. Statistical analyses were performed using GraphPad Prism program. Similar analysis of compounds 3b and 4b is shown in FIGS. 9A-9C.

Figure 8:
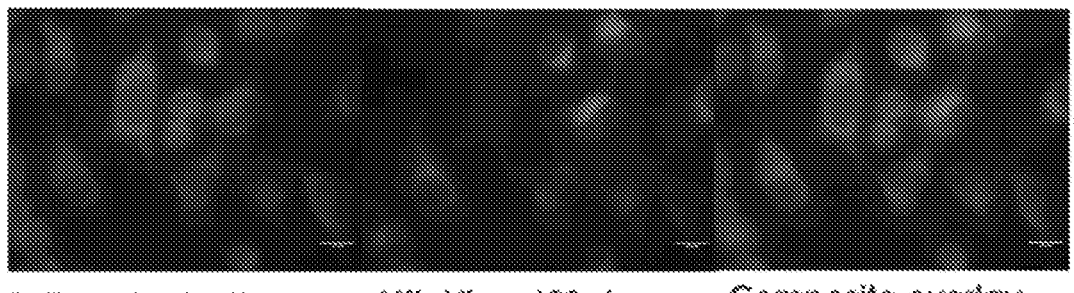
FIG. 8. Fluorescent microscopy analysis of localization of compounds (sulfone derivative of MA-1) was analyzed to determine where in the cell that the compound localizes.
Figure 10:
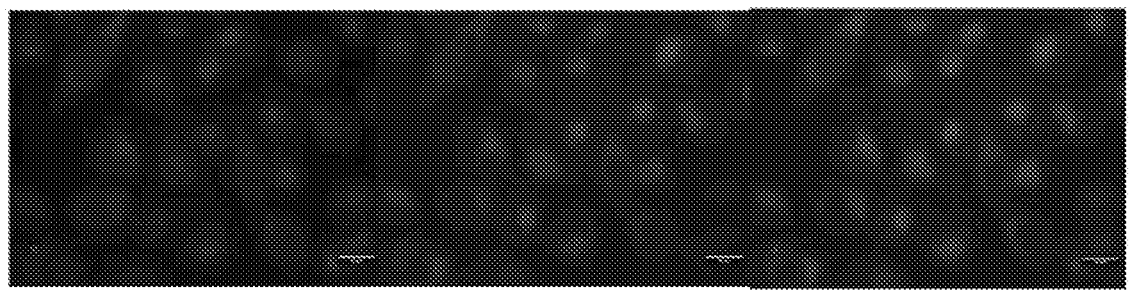
FIG. 10. Fluorescent microscopy analysis of localization of compounds (sulfone derivative of Compound 3b) was analyzed to determine where in the cell that the compound localizes.

The localization of these compounds was analyzed by microscopy in FIGS. 8 and 10. These compounds were shown to localize into the mitochondria.

Finally, compounds MA-1 (1a) and MA-2 (1b) show that in the presence of UV-A irradiation led to cell cycle progression is arrested while when the compound is administered in the absence of UV or after the cell has been irradiated then the progression of the cell cycle is not arrested.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. REFERENCES

The following references, to the extent that they provide exemplary procedural or other details supplementary to those set forth herein, are specifically incorporated herein by reference:

Allred and Liebeskind, *J. Am. Chem. Soc.*, 118:2748-2749, 1996.
Altman & Richheimer, *Tetrahedron Lett.*, 49:4709, 1971.
Altmann et al., *Progress in the Chemistry of Organic Natural Products*, 90; 2009.
Balasubramanian et al., *Bioorg. Med. Chem. Lett.*, 18:2996, 2008.
Balasubramanian et al., *J. Med. Chem.*, 52:238, 2009.
Barton et al., *J. Chem. Soc. Perkin. Trans.* 1, 159, 1982.
Blanco et al., *Bioorg. Med. Chem.*, 25 (19), 5050-5054, 2017.
Borowiak et al., *Cell*, 162 (2), 403-411, 2015.
Braig et al., *Cell Death Dis.*, 5:e1001, 2014.
Burkhart & Kazmaier, *RSC Advances*, 2:3785, 2012.
Burkhart et al., *Eur. J. Org. Chem.*, 3050, 2011.
Chai et al., *Chem. Biol.*, 17:296, 2010.
Chari et al., *Angew. Chem. Int. Ed.*, 53:3796-3827, 2014.
Chari et al., *Angew. Chem., Int. Ed.*, 53:3796, 2014
Chatgilialoglu et al., *Chem. Rev.*, 99:1991, 1999.
Cohen et al., *S. Cancer Res.*, 74:5700, 2014.
Colombo et al., *J. Org. Chem.*, 81:10302, 2016.
Corey & Helal, *Angew. Chem., Int. Ed.*, 37:1986, 1998.
Corey et al., *Am. Chem. Soc.*, 109: 5551, 1987.
Cormier et al., *EMBO Rep*, 9:1101, 2008.
Cosp et al., *Tetrahedron Letters*, 51:2391-2393, 2001.
Cui et al., *Bioorg. Med. Chem. Lett.*, 15:4130, 2005.
de Carne-Carnavalet et al., *Org. Lett.*, 13:956-959, 2011.
Deloux & Srebnik, *Chem. Rev.*, 93:763, 1993.
Desnoyers et al., *Sci. Transl. Med.*, 5:207ra144, 2013.
Dömling et al., *Angew. Chem., Int. Ed.*, 45:7235, 2006.
Dömling, W. *Mol. Diversity*, 9:141, 2005.
Dosio et al., *Recent Pat. Anti Canc.*, 9:35-65, 2014.
Eberele et al., *Helv. Chim. Acta*, 81:182, 1998.
Eberele et al., *Helv. Chim. Acta*, 81:182, 1998.
Eberle & Keese, *Helv. Chim. Acta*, 93: 1583, 2010.
Eberle et al., *Helv. Chim. Acta*, 93:1583, 2010.
Eirich et al., *Mol. BioSyst.*, 8:2067, 2012.
Elnakady et al., *Biochem. Pharmacol.*, 67:927-935, 2004.
EP 2 174 947 A1
EP 2 409 983 A1, 2012
Falkiner et al., *Org. Process Res. Dev.*, 17:1503, 2013.
Floyd et al., *ChemMedChem*, 6:49, 2011.
Friestad et al., *J. Antibiot.*, 69:294, 2016.
Fulmer et al., *Organometallics*, 29:2176, 2010.
Ftirstner et al., *Angew. Chem. Int. Ed.*, 45:5510-5515, 2006.
Gerber et al., *Nat. Prod. Rep.*, 30:625-639, 2013.
Ghanem and Aboul-Enein, *Chirality*, 17:1-15, 2005.
Guillena et al., *Chem. Rev.*, 110:1611, 2010.
Hartung et al., *Synthesis*, 12:1844-1850, 2003.
Herrmann et al., *PLoS ONE*, 7:e37416, 2012.
Hin et al., *J. Org. Chem.*, 67:7365, 2002.
Hoffmann et al., *Org. Biomol. Chem.*, 13:6010, 2015.
Höfle et al., *Pure Appl. Chem.*, 75:167, 2003.
Höfle, In Wissenschaftlicher Ergebnisbericht, Druckerei and Verlag GmbH: Braunschweig-Stöckheim, Germany, p 101-104, 1999/2000.
Hopkins & Wipf, *Nat. Prod. Rep.*, 26:585-601, 2009.
Hopkins et al., *Org. Lett.*, 13:4088-4091, 2011.
In et al., *Arch. Pharm. Res.* 30:695, 2007.
Ingalsbe et al., *Synthesis*, 1: 98, 2010.
Irschik et al., *J. Antibiot.*, 48 31-35, 1995.
Jansen et al., *Liebigs Ann. Chem.*, 759-773, 1994.
Jordan et al., *Med. Res. Rev.*, 18 (4), 259-296, 1998.
Kazmaier et al., *Open Nat. Prod. J.*, 6:12, 2013.
Kerr et al., *J. Org. Chem.*, 70:5725, 2005.
Khalil et al., *ChemBioChem*, 7:678, 2006.
Khemnar et al., *Synlett*, 25: 110, 2014.
Korang et al., *J. Am. Chem. Soc.*, 132 (12), 4466-4476, 2010.
Kubicek et al., *Angew. Chem., Int. Ed.*, 49:4809, 2010.
Kubisch et al., *J. Nat. Prod.*, 77:536, 2014.
Lee et al., *Org. Prep. Proc. Int.*, 28:480, 1996.
Lee et al., *Org. Prep. Proc. Int.*, 28:480, 1996.
Leverett et al., *C. ACS Med. Chem. Lett.*, 7: 999, 2016.
Li et al., *ACS Appl. Mater. Interfaces*, 9 (20), 16793-16802, 2017.
Liu et al., *ChemCatChem*, 8:1043, 2016.
López et al., *J. Org. Chem.*, 70:6346-6352, 2005.
Matcha et al., *Angew. Chem., Int. Ed.*, 52:2082, 2013.
Murray et al., *Nat. Prod. Rep.*, 32:654, 2015.
Myers et al., *J Org. Chem.*, 62:7507-7507, 1998.
Nagao et al., *J Org. Chem.*, 51:2391-2393, 1986.
Neri et al., *ChemMedChem.*, 1:175, 2006.
Nicolaou et al., *Angew. Chem. Int. Ed.*, 44:1378-1382, 2005.
Nicolaou et al., *Angew. Chem., Int. Ed.*, 44:1378, 2005.
Nicolaou et al., *ChemMedChem*, 11:31, 2016.
Nicolaou et al., D. *J. Am. Chem. Soc.*, 138, 1698, 2016.
Nicolaou et al., *J. Am. Chem. Soc.*, 138:1698, 2016.
Nicolaou, *Chem. Biol.*, 21:1031-1045, 2014.
Pando et al., *J. Am. Chem. Soc.*, 133:7692, 2011.
Pando et al., *Org. Lett.*, 11:5567, 2009.
Pangbom et al., *Organometallics*, 15:1518, 1996.
Park et al., *Bioorg. Med. Chem.*, 23:6827, 2015.
Park et al., *Synlett*, 26:1063, 2015.
Patterson et al., *Chem.-Eur. J.*, 13:9534, 2007.
Patterson et al., *J Org. Chem.*, 73:4362, 2008.
Patzel et al., *Eur. J Org. Chem.*, 493, 2004.
Peltier et al., *A. J Am. Chem. Soc.*, 128:16018, 2006.
Perez et al., *Drug Disc. Today*, 19:869, 2014.
Phillips et al., *Org. Lett.*, 2:1165-1168, 2000.
Polu & Lowman, *Expert Opin. Biol. Ther.*, 14:89, 2014.
Preze et al., *Drug Disc. Today*, 19:869, 2014.
Pulukuri et al., *Org. Lett.*, 16:2284-2287, 2014.
Raghavan et al., *J. Med. Chem.*, 51:1530, 2008.
Rath et al., *J Pharmacol.*, 167:10482012.
Reetz et al., *Tetrahedron: Asymmetry*, 3:1377, 1992.
Ross et al., *Biochemistry. (Mosc).*, 70 (2), 222-230, 2005.
Sandmann et al., *Chem. Biol.*, 11:1071 2014.
Sani et al., *Angew. Chem., Int. Ed.*, 46:3526, 2007.
Sani et al., *Chem.-Eur. J.*, 23:5842, 2017.
Sapra & Shor, *Pharmacol. Ther.*, 138:452-469, 2013.
Sasse & Menche, *Nat. Chem. Biol.*, 3:87, 2007.
Sasse et al., *J. Antibiot.*, 53:879, 2000.
Schackel et al., *Angew. Chem., Int. Ed.*, 49:1619-1622, 2010.
Scheidt et al., *J. Org. Chem.*, 63:6436-6437, 1998.
Schmidt et al., *Synthesis*, 487, 1992.
Shankar et al., *Org. Biomol. Chem.*, 11: 2273, 2013.
Shankar et al., *Synlett*, 1673, 2011.
Shankar et al., *Tetrahedron Lett.*, 54:6137, 2013.
Sheldon et al., *Org. Biomol. Chem.*, 14 (1), 40-49, 2016.
Shibue et al., *Bioorg. Med. Chem. Lett.*, 21:431, 2011.

Shibue et al., *Chem.-Eur. J.*, 16:11678, 2010.
Sievers & Senter, *Annu. Rev. Med.*, 64:15, 2013.
Sievers & Senter, *Annu. Rev. Med.*, 64:15-29, 2013.
Smrcina et al., *Tetrahedron*, 53:12867, 1997.
Sohtome et al., *Angew. Chem., Int. Ed.*, 49:7299, 2010
Soroka et al., *Bioorg. Med. Chem. Lett.*, 16:4777, 2006.
Steinmetz et al., *Angew. Chem., Int. Ed.*, 43:4888, 2004.
Stepan et al., *J Med. Chem.*, 55:3414, 2012.
Still et al., *J. Org. Chem.* 43:2923, 1978.
Szymanski et al., *Chemistry*, 21 (46), 16517-16524, 2015.
Tao et al., *Tetrahedron*, 72:5928, 2016.
Throgmorton et al., *J Heterocycl. Chem.*, 54 (6), e3002, 2017.
Trnka et al., *PLoS One*, 10 (4), e0121837, 2015.
Tumey et al., *ACS Med. Chem. Lett.*, 7:977, 2016.
Ullrich et al., *Angew. Chem., Int. Ed.*, 48:4422, 2009.
Ullrich et al., *Angew. Chem., Int. Ed.*, 48:4422, 2009.
Ullrich et al., *Eur. J. Org. Chem.*, 6367, 2009.
US 2010/0240701 A1
US 2011/0027274 A1
US 20110312996 A1
US 20110312996 A1, 2011
US 2016/0130299 A1
U.S. Pat. No. 7,816,377 B2, 2010
Vlahov et al., *Bioorg. Med. Chem. Lett.*, 21:6778, 2011.
Wang and Lin, *Organometallic*, 29:3077-3084, 2010.
Wang et al., *Chem. Biol. Drug Des.*, 70:75, 2007.
Wang et al., *Chin. J Chem.*, 31:40, 2013.
Wang et al., *Mol. Pharmacol.*, 89:233, 2016.
Wipf & Graham, *Org. Biomol. Chem.*, 3:31-35, 2005.
Wipf & Wang, *Org. Lett.*, 9:1605, 2007.
Wipf & Wang, Z. *Org. Lett.*, 9:1605, 2007.
Wlochal et al., *Org. Lett.*, 16:4094, 2014
WO 2004/005326 A2
WO 2004/005327, 2004
WO 2008/028934
WO 2008/106080 A2
WO 2009/012958 A2, 2009
WO 2009/055562 A1
WO 2012/010287 A1
WO 2012/019123 A1
WO 2013/149185 A1
WO 2014/160360 A1
WO 2017/031209 A1
Wu et al., *Oncotarget*, 6:40866-40879, 2015.
Xu et al., *Mini Rev. Med. Chem.*, 11:1572, 2013.
Yang et al., *Chem. Asian J.*, 8:1213, 2013.
Yang et al., *Tetrahedron Lett.*, 54:2986, 2013.
Yeung & Dong, *Chem. Rev.*, 111:1215, 2011.
Zeino et al., *J. Biosci. Med.*, 3:37, 2013.
Zheng et al., *Photochem. Photobiol. Sci. An Int. J.*, 791-800, 2016.

What is claimed:

1. A compound of formula:

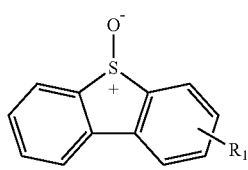

(I)

wherein:
$R_1$ is $-Y_1-R_2$; wherein:
$Y_1$ is C1-C6 alkanediyl, substituted C1-C6 alkanediyl, or a linker of the formula:

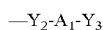

wherein:
$Y_2$ and $Y_3$ are each independently C1-C6 alkanediyl or substituted C1-C6 alkanediyl;
$A_1$ is $-C(O)O-$ or $-C(O)NH-$; and
$R_2$ is $P(R_3)(R_3')(R_3'')^+X_1^-$; wherein:
$R_3$, $R_3'$, and $R_3''$ are each independently C6-C12 aryl or substituted C6-C12 aryl; and
$X_1''$ is a monovalent anion;
or a pharmaceutically acceptable salt thereof.

2. The compound of claim 1 further defined as:

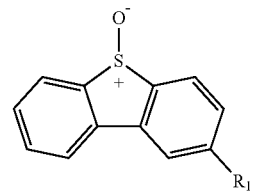

(II)

wherein:
$R_1$ is $-Y_1-R_2$; wherein:
$Y_1$ is C1-C6 alkanediyl or substituted C1-C6 alkanediyl; and
$R_2$ is $P(R_3)(R_3')(R_3'')^+X_1^-$; wherein:
$R_3$, $R_3'$, and $R_3''$ are each independently C6-C12 aryl or substituted C6-C12 aryl(e-12); and
$X_1^-$ is a monovalent anion;
or a pharmaceutically acceptable salt thereof.

3. The compound of claim 1, wherein $Y_1$ is C1-C6 alkanediyl.

4. The compound of claim 1, wherein $R_3$, $R_3'$, and $R_3''$ are each independently C6-C12 aryl.

5. The compound of claim 1, wherein the compound is further defined as:

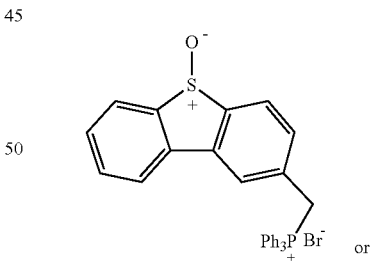

or

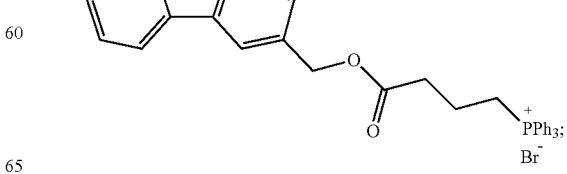

or a pharmaceutically acceptable salt thereof.

6. A method of making a compound of formula:

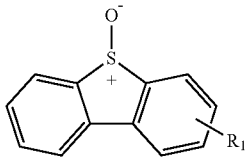

(I)

wherein:
R₁ is —Y₁—R₂; wherein:
C1-C6 alkanediyl, substituted C1-C6 alkanediyl, or a linker of the formula:

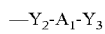

wherein:
Y₂ and Y₃ are each independently C1-C6 alkanediyl or substituted C1-C6 alkanediyl;
A₁ is —C(O)O— or —C(O)NH—; and
R₂ is P(R₃)(R₃')(R₃")⁺X₁⁻; wherein:
R₃, R₃', and R₃" are each independently C6-C12 aryl or substituted C6-C12 aryl; and
X₁⁻ is a monovalent anion;
comprising:
(A) reacting a compound of the formula:

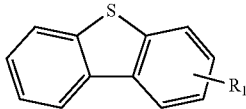

(III)

wherein:
R₁ is —Y₁—R₂'; wherein:
Y₁ is C1-C6 alkanediyl, substituted C1-C6 alkanediyl, or a linker of the formula:

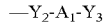

wherein:
Y₂ and Y₃ are each independently C1-C6 alkanediyl or substituted C1-C6 alkanediyl;
A₁ is —C(O)O— or —C(O)NH—; and
R₂' is halo;
in the presence of an oxidizing agent to form a compound of the formula:

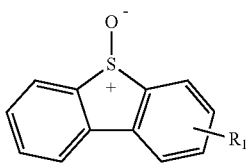

(I)

wherein:
R₁ is —Y₁—R₂'; wherein:
Y₁ is C1-C6 alkanediyl, substituted C1-C6 alkanediyl, or a linker of the formula:

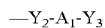

wherein:
Y₂ and Y₃ are each independently C1-C6 alkanediyl or substituted C1-C6 alkanediyl;
A₁ is —C(O)O— or —C(O)NH—; and
R₂' is halo; and
(B) reacting the compound prepared in step A with a compound of the formula:

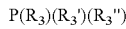

wherein:
R₃, R₃', and R₃" are each independently C6-C12 aryl or substituted C6-C12 aryl.

7. A compound of formula:

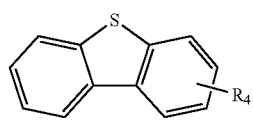

(III)

wherein:
R₄ is—Y₄-R₅; wherein:
Y₄ is a linker of the formula:

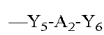

wherein:
Y₅ and Y₆ are each independently C1-C6 alkanediyl or substituted C1-C6 alkanediyl;
A₂ is —C(O)O— or —C(O)NH—; and
R₅ is P(R₆)(R₆')(R₆")⁺X₂⁻; wherein:
R₆, R₆', and R₆" are each independently C6-C12 aryl or substituted C6-C12 aryl; and
X₂⁻ is a monovalent anion;
or a pharmaceutically acceptable salt thereof.

8. The compound of claim 7, wherein R₆, R₆', and R₆" are each independently C6-C12 aryl.

9. The compound of claim 7, wherein X₂⁻ is halide.

10. The compound of claim 7, wherein the compound is further defined as:

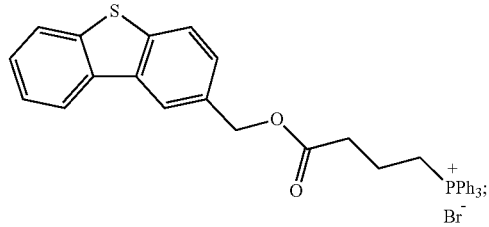

or a pharmaceutically acceptable salt thereof.

11. A pharmaceutical composition comprising a compound of claim 7 and an excipient.

12. A method of treating a cancer in a patient having said cancer comprising (a) administering to the patient a therapeutically effective amount of a compound or composition of claim 1, and (b) exposing a cancer cell in said patient to UV-A light.

13. The method of claim 12, wherein the cancer is a carcinoma, sarcoma, lymphoma, leukemia, melanoma, mesothelioma, multiple myeloma, or seminoma.

14. The method of claim 12, wherein the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

15. The method of claim 12, wherein UV-A light is 320-400 nm light.

16. A method of treating a cancer in a patient having said cancer thereof comprising administering to the patient a therapeutically effective amount of a compound or composition of claim 7.

17. The method of claim 16, wherein the cancer is a carcinoma, sarcoma, lymphoma, leukemia, melanoma, mesothelioma, multiple myeloma, or seminoma.

18. The method of claim 16, wherein the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

\* \* \* \* \*

UNITED STATES PATENT AND TRADEMARK OFFICE
CERTIFICATE OF CORRECTION

| | | |
|---|---|---|
| PATENT NO. | : 12,054,470 B2 | Page 1 of 1 |
| APPLICATION NO. | : 17/046885 | |
| DATED | : August 6, 2024 | |
| INVENTOR(S) | : McCulla et al. | |

It is certified that error appears in the above-identified patent and that said Letters Patent is hereby corrected as shown below:

In the Claims

Claim 1, Column 32, Line 14, "$X_1'''$" should be --$X_1^-$--.

Signed and Sealed this
Tenth Day of September, 2024

Katherine Kelly Vidal
*Director of the United States Patent and Trademark Office*